US009503681B1

(12) United States Patent
Popescu et al.

(10) Patent No.: US 9,503,681 B1
(45) Date of Patent: Nov. 22, 2016

(54) SIMULATED TRANSPARENT DISPLAY WITH AUGMENTED REALITY FOR REMOTE COLLABORATION

(71) Applicant: Purdue Research Foundation, West Lafayette, IN (US)

(72) Inventors: Voicu S Popescu, West Lafayette, IN (US); Juan P Wachs, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 15/167,011

(22) Filed: May 27, 2016

Related U.S. Application Data

(60) Provisional application No. 62/168,438, filed on May 29, 2015.

(51) Int. Cl.
| | | |
|---|---|---|
| *H04N 7/14* | (2006.01) | |
| *G06T 7/00* | (2006.01) | |
| *G06T 19/00* | (2011.01) | |
| *G06K 9/62* | (2006.01) | |
| *G06T 7/20* | (2006.01) | |
| *G06F 17/24* | (2006.01) | |
| *G06F 19/00* | (2011.01) | |

(52) U.S. Cl.
CPC ............. *H04N 7/141* (2013.01); *A61B 90/37* (2016.02); *G06F 17/241* (2013.01); *G06F 19/3425* (2013.01); *G06K 9/6215* (2013.01); *G06T 7/0042* (2013.01); *G06T 7/0051* (2013.01); *G06T 7/20* (2013.01); *G06T 19/006* (2013.01); *A61B 2090/373* (2016.02)

(58) Field of Classification Search
CPC ....................................................... H04N 7/14

USPC ......... 348/14.01, 14.02, 14.03, 14.05, 14.07, 348/14.14
See application file for complete search history.

(56) References Cited

U.S. PATENT DOCUMENTS

| | | | | |
|---|---|---|---|---|
| 2008/0117225 | A1* | 5/2008 | Wegenkittl | A61B 6/461 345/581 |
| 2011/0251483 | A1* | 10/2011 | Razzaque | A61B 6/466 600/424 |
| 2013/0093829 | A1* | 4/2013 | Rosenblatt | G09B 5/00 348/14.01 |
| 2014/0176661 | A1* | 6/2014 | Smurro | G06T 9/001 348/14.06 |
| 2014/0198190 | A1* | 7/2014 | Okumu | G02B 27/017 348/53 |

(Continued)

OTHER PUBLICATIONS

Baricevic et al. "User-Perspective Augmented Reality Magic Lens from Gradients" in the Proceedings of the 20th ACM Symposium on Virtual Reality Software and Technology, Nov. 11, 2014, pp. 87-96.

(Continued)

*Primary Examiner* — Olisa Anwah
(74) *Attorney, Agent, or Firm* — Lee & Hayes, PLLC; Shigeharu Furukawa; Christopher J. White

(57) ABSTRACT

A method and system for remote collaboration and remote instruction utilizing computing devices at trainee site and mentor sites are disclosed. Annotations are superimposed onto a trainee's view of a view field displayed using a simulated transparent display with augmented reality ("AR"). By tracking the position of the trainee's view point, the position of the trainee's computing device, and the geometry of the view field, the annotations remain anchored to the image of the view field when the trainee device moves and/or when the view field deforms or becomes occluded.

20 Claims, 11 Drawing Sheets

(56) References Cited

U.S. PATENT DOCUMENTS

| | | | | |
|---|---|---|---|---|
| 2014/0267658 A1* | 9/2014 | Speier | .................... | H04N 7/181 348/72 |
| 2016/0191887 A1* | 6/2016 | Casas | ................. | H04N 13/0011 348/47 |
| 2016/0212370 A1* | 7/2016 | Lee | .................... | H04N 5/44591 |

OTHER PUBLICATIONS

Ereso, et al., "Live Transference of Surgical Subspecialty Skills Using Telerobotic Proctoring to Remote General Surgeons" in the Journal of the American College of Surgeons, vol. 211, No. 3, Sep. 30, 2010, pp. 400-411.

Loescher, et al., "An Augmented Reality Approach to Surgical Telementoring," in the Proceedings of the 2014 IEEE International Conference on Systems, Man and Cybernetics (SMC), Oct. 5, 2014, pp. 2341-2346.

Shenai, et al., "Virtual Interactive Presence and Augmented Reality (VIPAR) for Remote Surgical Assistance", in the Jounal of Operative Neurosurgery, No. 68, Mar. 1, 2011, 8 pages.

Unuma, et al., "See-through Mobile AR System for Natural 3D Interaction", in the Proceedings of the ACM Companion Publication of the 19th International Conference on Intelligent User Interfaces, Feb. 24, 2014, pp. 17-20.

* cited by examiner

1100

1102 → 1: Annotation points: $A = \{(x_{ak}, y_{ak})\}, k \in [1, v]$
1104 → 2: Template feature points: $T = \{(x_{ti}, y_{ti}, f_{ti})\}, i \in [1, m]$
1106 → 3: Scene feature points: $S = \{(x_{sj}, y_{sj}, f_{sj})\}, j \in [1, n]$ 1108 {
    4:   for $i \in [1, m]$ do
    5:       for $j \in [2, n]$ do
    6:           if $f_{ti} \simeq f_{sj}$ then
    7:               $q \leftarrow (i, j)$
    8:           end if
    9:       end for
}

1110 {
    10:       if $q$ exists then
    11:           $M \leftarrow q$
    12:       end if
}

1112 → 13: end for

1202 → 1: Top-left crop point for template: $(x_c, y_c)$ 1204
2: for $(i, j) \in M$ do
3:   for $(\hat{i}, \hat{j}) \in M$ where $index(\hat{i}, \hat{j}) > index(i, j)$ do
4:     $D_T \leftarrow \sqrt{(x_{ti} - x_{t\hat{i}})^2 + (y_{ti} - y_{t\hat{i}})^2}$
5:     $D_S \leftarrow \sqrt{(x_{si} - x_{s\hat{i}})^2 + (y_{si} - y_{s\hat{i}})^2}$
6:     $\theta \leftarrow \tan^{-1}\left(\dfrac{x_{t\hat{i}} - x_{t\hat{i}}}{y_{t\hat{i}} - y_{t\hat{i}}}\right) - \tan^{-1}\left(\dfrac{x_{s\hat{i}} - x_{s\hat{i}}}{y_{s\hat{i}} - y_{s\hat{i}}}\right)$
7:   end for
8: end for

1206
9: $\bar{d}_t \leftarrow median(D_T); \bar{d}_s \leftarrow median(D_S)$
10: $r \leftarrow \dfrac{\bar{d}_s}{\bar{d}_t}$ 1208
11: $a \leftarrow median(\theta)$
12: $\bar{x}_t \leftarrow mean(x_t); \bar{y}_t \leftarrow mean(y_t); \bar{x}_s \leftarrow mean(x_s);$
    $\bar{y}_s \leftarrow mean(y_s)$
13: Project points $\in A$ using Equation (1)

1210

$$P_k = \left(\hat{x}_s - \dfrac{\cos(\alpha)(-x_{ak} + x_c + \hat{x}_t)}{r} + \dfrac{\sin(\alpha)(-y_{ak} + y_c + \hat{y}_t)}{r}\right),$$
$$\left(\hat{y}_s - \dfrac{\sin(\alpha)(-x_{ak} + x_c + \hat{x}_t)}{r} + \dfrac{\cos(\alpha)(-y_{ak} + y_c + \hat{y}_t)}{r}\right)$$

SIMULATED TRANSPARENT DISPLAY WITH AUGMENTED REALITY FOR REMOTE COLLABORATION

CROSS-REFERENCE TO RELATED APPLICATIONS

This application is a non-provisional of, and claims priority to and the benefit of, U.S. Provisional Patent Application Ser. No. 62/168,438, filed May 29, 2015 and entitled "AUGMENTED REALITY TRANSPARENT DISPLAY FOR TELEMENTORING AND TELEPROCTORING," the entirety of which is incorporated herein by reference.

STATEMENT OF FEDERALLY SPONSORED RESEARCH OR DEVELOPMENT

This invention was made with government support under W81XWH-14-1-0042 awarded by the US. Army Medical Research Acquisition Activity. The government has certain rights in the invention.

TECHNICAL FIELD

The present disclosure generally relates to displays, and in particular to systems and methods for enhancing remote collaboration using simulated transparent displays with augmented reality.

BACKGROUND

Remote collaboration and remote instruction have a number of useful applications such as telementoring. One example of telementoring is surgical telementoring, which has the potential to abstract away the geographic distance between a patient in need of expert surgical care and the surgeon with the required expertise. For example, if a patient urgently needing a complex procedure for which a rural hospital does not have a specialist, telementoring could enable the rural surgeon to perform the procedure under the guidance of a remote expert, without the delays associated with transporting the patient to a major surgical center. If a surgeon were deployed to a location where its operating base has limited resources, the surgeon could provide urgent specialized surgical care with the help of an expert surgeon remotely located, possibly thousands of miles away. Further, if an innovative surgical technique were available but not yet widely adopted, a surgeon could disseminate the novel procedure through telementoring.

However, the current systems fall short of realizing the possible potential of surgical telementoring. In the current systems, a remote mentor might annotate a video feed of a surgical operation using a telestrator. The annotated video is sent back to the operating room where it is displayed on a nearby monitor, then a local surgeon performing the operation needs to shift focus frequently between the operating field and the nearby monitor to acquire and apply the instructions from the remote mentor. The local surgeon first has to parse and understand the instructions on the monitor, memorize the instructions, and finally after shifting his focus back to the surgery, the local surgeon has to, temporally and spatially, project those instructions into the real-world context of the surgery. This indirect approach to acquiring and applying mentor instructions translates to a significant additional cognitive load for the trainee and interferes with natural hand-eye coordination, which can lead to surgery delays or even errors. Further, the annotations used in the current systems are static and can become disassociated from the operating field elements for which they were associated. For example, an incision line drawn by the remote mentor can move away from its intended location as the operating field changes.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items.

FIG. 1 is an example keypoint matching algorithm in accordance with at least one aspect of the present disclosure.

FIG. 12 is an example parameter extraction algorithm in accordance with at least one aspect of the present disclosure.

DETAILED DESCRIPTION

Figure 1:
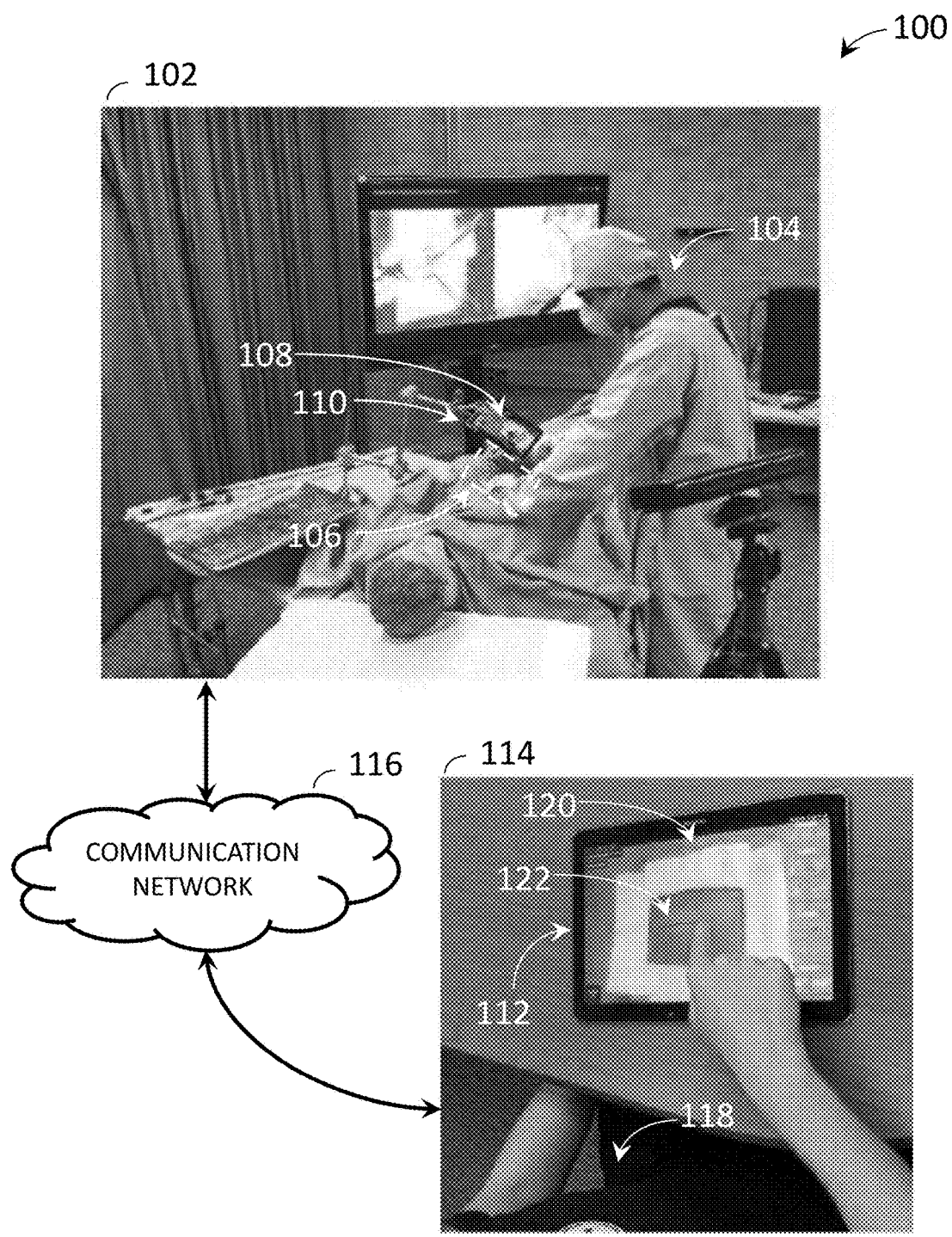
FIG. 1 is a graphical representation of annotated photographs of components of an example environment of a telementoring system in accordance with at least one aspect of the present disclosure.

The present disclosure provides, in various aspects, an apparatus, method and system for remote collaboration and remote instructions. Example embodiments in accordance with the present disclosure includes telementoring which can, e.g., remotely provide enhanced instructions, e.g., surgical telementoring, which can be used to demonstrate an apparatus, method and system. In the embodiments, the annotations are superimposed directly onto an image of a view field where telementoring or telecorroboration is desired such as a surgery area, using a simulated transparent display with augmented reality ("AR"). Telemedicine and telementoring applications rely on effective communication of medical expertise. AR has potential of enhancing telementoring either as an interface or as an environment. For example, a virtualized interface may allow for more intuitive interaction between an operating surgeon and relevant medical information provided. In laparoscopic surgery where the operating surgeon and the telementoring surgeon can share the same real-time laparoscopic video, the live video, which is the image of the view field, may be displayed to the telementoring surgeon in conjunction with a view of the operating room. Additional viewpoints may provide greater visual context to both trainee and mentor.

The fundamental challenge in using AR in surgical environments and other telementoring environments is integrating synthetic overlays seamlessly within a real-world scene. Many existing systems would require the trainee to look at a screen with a display that does not align with the trainee's actual view of the scene outside the screen. Systems that use AR head-mounted displays may interfere with the vision or the trainee's head motion and cause ocular fatigue. In addition, it is important for an augmented image to avoid obscuring important real-world detail, while ensuring that the information provided by the AR is readily accessible to the trainee.

Generally, any function, component, device, module, system and alike herein described may not be limited to a physical component but may also be realized with a set of executable instructions stored in a non-transitory memory device, e.g., a computer-readable memory, to be executed by one or more processors, or be realized with a combination of one or more physical components with such instructions.

Computer-readable media described herein include computer storage media and/or communication media. Computer storage media includes tangible storage units such as volatile memory, nonvolatile memory, and/or other persistent and/or auxiliary computer storage media, removable and non-removable computer storage media implemented in any method or technology for storage of information such as computer-readable instructions, data structures, program modules, or other data. Computer storage media includes tangible or physical forms of media included in a device or hardware component that is part of a device or external to a device, including but not limited to random access memory (RAM), static random-access memory (SRAM), dynamic random-access memory (DRAM), phase change memory (PRAM), read-only memory (ROM), erasable programmable read-only memory (EPROM), electrically erasable programmable read-only memory (EEPROM), flash memory, compact disc read-only memory (CD-ROM), digital versatile disks (DVDs), optical cards or other optical storage media, magnetic cassettes, magnetic tape, magnetic disk storage, magnetic cards or other magnetic storage devices or media, solid-state memory devices, storage arrays, network attached storage, storage area networks, hosted computer storage or memories, storage, devices, and/or storage media that can be used to store and maintain information for access by a computing device 102 or 104.

In contrast to computer storage media, communication media can embody computer-readable instructions, data structures, program modules, or other data in a modulated data signal, such as a carrier wave, or other transmission mechanism. As defined herein, computer storage media does not include communication media.

The terms "local" and "remote" do not imply any specific distance between the operator and the instructor; various aspects are useful with any positive, nonzero distance between the operator and the instructor.

FIG. 1 is an example telementoring system environment 100 in accordance with at least one aspect of the present disclosure. At the local surgeon site, or trainee site, 102, the local surgeon, or a trainee, 104 sees the view field 106 as the annotated view field 108 on a trainee system 110, shown as a simulated transparent display device, suspended in his field of view. The trainee system 110 is connected to a remote mentor system 112 located at a remote mentor site 114 via a communication network 116. A remote mentor 118 sees an image 120 of the view field 106, and enters an annotation 122 to the remote mentor system 112. Information related to the annotation 122 is communicated to the trainee system 110 via the communication network 116, and an appropriate annotation is displayed on the trainee system 110 in real, or near real, time.

Figure 2:
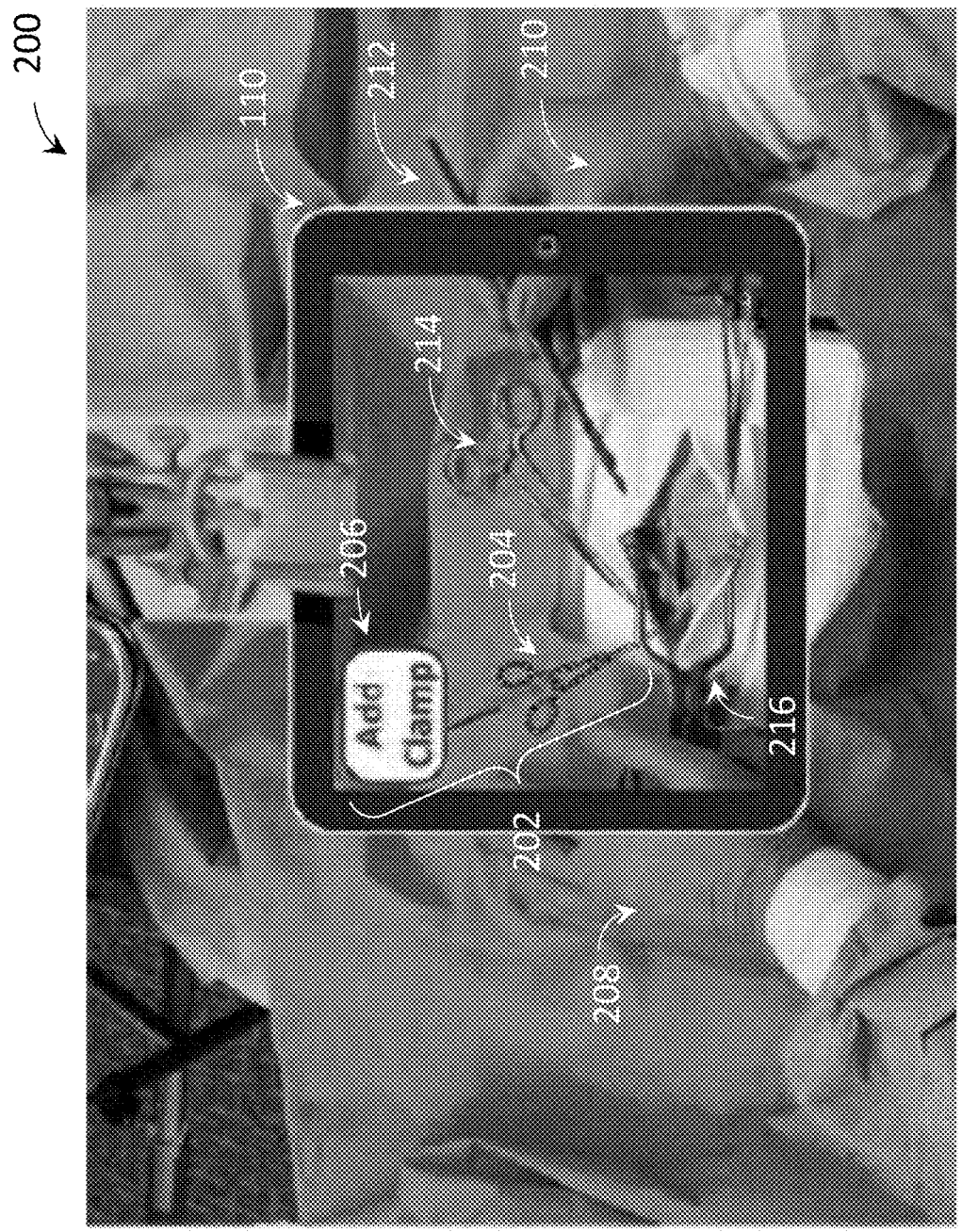
FIG. 2 is a graphical representation of an example view of a simulated transparent display with augmented reality by the trainee as used in FIG. 1 in accordance with at least one aspect of the present disclosure.

FIG. 2 is an example view 200 by the trainee 104 of the view field 106 and the surrounding areas in accordance with at least one aspect of the present disclosure. The trainee's view includes the trainee system 110 showing a live image of the view field 106 under the trainee system 110 except for the area where the annotation 202 created by a remote mentor is displayed. In this view, the annotation 202 indicates the precise placement of an additional surgical clamp 204 along with the instructions 206 to "Add Clamp." The simulated transparent display image of the view field 106 displayed on the trainee system 110 represents, or simulate, a direct view of the view field 106 seen by the trainee 104, allowing the trainee 104 to see his hands 208, 210, the surgical instruments 212, 214, 216, and the actual view field 106 under the trainee system 110 as if seeing through the trainee system 110. The part of the view field 106 seen by the trainee 104 through the trainee system 110 is continued with the surrounding region of the view field 106 that the trainee 104 sees directly. The annotation 202 remains anchored to the view field elements for which they were defined even as the trainee system 110 is repositioned, as the head position of the trainee 104 changes, and/or as the view field 106 changes over time. The simulated transparent display with augmented reality approach has the potential to bypass the shortcomings of the conventional telestrator-based approach by integrating annotations into the view field, allowing the local surgeon to benefit from the annotations without shifting focus. The alignment between the displayed image and the peripheral regions of the view field preserves the natural hand-eye coordination on which surgeons rely. The annotations are anchored to the view field elements and remain anchored to the elements as the viewpoint and/or view field change causing the elements to shift or move. The anchoring of the annotations to the elements reduces the need for the remote mentor to redraw annotations that have drifted out of place, improving the continuity of the visual guidance provided to the trainee.

The functions and utilities of the simulated transparent display 110 at the trainee site may be accomplished by using a conventional tablet that is capable of displaying the live image, or video stream, acquired by its back-facing camera. The live image may be sent wirelessly to the mentor site where it is displayed on the mentor's tablet. Using the tablet's touch-based user interface, the mentor may add graphical and textual annotations to a frame of the video stream. The annotations are sent back to the trainee site where they are overlaid on the trainee's tablet display to provide guidance to the trainee.

Figure 3:
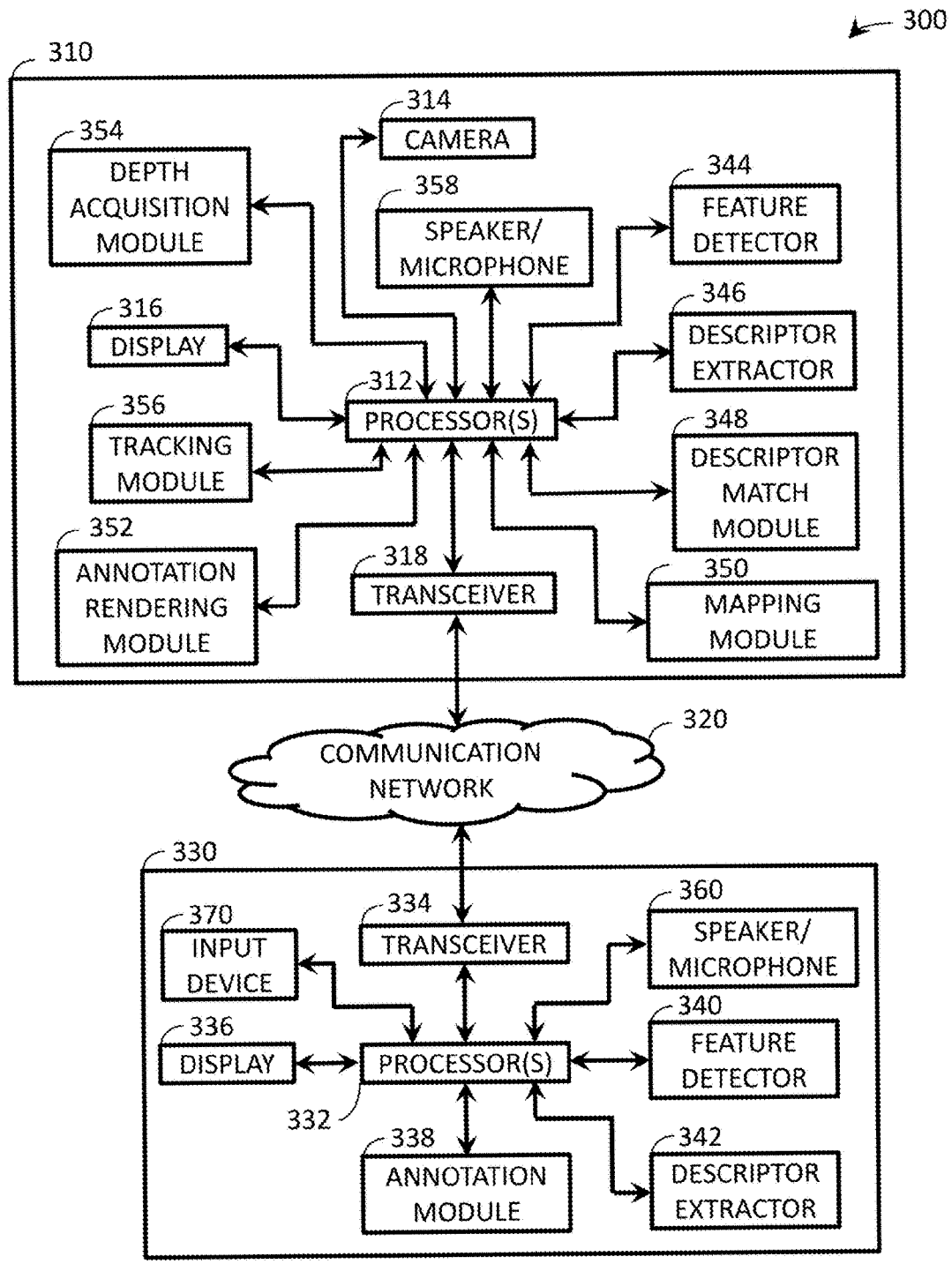
FIG. 3 is an example block diagram of an embodiment of an enhanced remote collaboration system, e.g., using a simulated transparent display with augmented reality, in accordance with at least one aspect of the present disclosure.

FIG. 3 is an example block diagram 300 of an embodiment of an enhanced remote collaboration system using a simulated transparent display with augmented reality in accordance with at least one aspect of the present disclosure. The trainee system 310 or other local computing device, shown as the display device 110 in FIGS. 1 and 2, may be implemented using a tablet. Although a tablet is used for example purposes, other types of a computing device equipped with a display and a camera, which may or may not be integrated in the computing device, may be utilized. A processor, or processors, 312 of the trainee system 310 may be coupled to various components and modules in the tablet 310 and enables functions associated with those components and modules. The modules can additionally or alternatively represent computer program instructions operable by the processor(s) 312 to perform the desired functions, or any combination of modules coupled to or operable by the processor(s) 312 to perform the desired functions.

A camera 314 of the trainee system 310 acquires a video stream of the view field 106, and displays each acquired frame on the display 316 of the trainee system 310. A transceiver 318 may wirelessly send each acquired frame through a communication network 320 to a remote mentor system 330 or other remote computing device to be processed for annotation anchoring. The communication network 320 may be any kind of communication network, wired or wireless, capable of communicating required data between the trainee system 310 and the remote mentor system 330, such as cellular, Wi-Fi, Bluetooth, Ethernet communication networks and alike.

The remote mentor system 330, which may be another computing device, comprises a processor, or processors, 332 which may be coupled to various components and modules of the remote mentor system 330 and enables functions associated with those components and modules. In the remote mentor system 330, a transceiver 334 receives the video stream comprising of continuously updated frames via the communication network 320, and each frame is sequentially displayed on a display 336 which may be a touchscreen. The display 336 at the remote mentor's site may also be a large screen device to project the life size, or enlarged size, of the view field.

In some examples, the remote mentor system 330 can include at least one input device 370, integral or peripheral to system 330. The at least one input device 370 can be user-operable. Examples of input devices 370 can include, e.g., a keyboard, keypad, a mouse, a trackball, a pen sensor or smart pen, a light pen or light gun, a game controller such as a joystick or game pad, a voice input device such as a microphone, voice-recognition device, or speech-recognition device, a touch input device, a gestural input device such as a touchscreen, a grip sensor, an accelerometer, another haptic input, a visual input device such as one or more cameras or image sensors, and the like. Input device 370 can be arranged with respect to, or operably coupled with, display 336 to provide a user interface via which the mentor can view images and provide annotations. For example, input device 370 can be a touch sensor overlaid on or otherwise associated with display 336 to form a touchscreen.

An annotation module 338 may present various annotation choices to the mentor via a user interface. The mentor may select a reference frame from the video stream and define selected annotations to the reference frame, e.g., by providing inputs via input device 370 of the user interface. The annotation module 338 generates and displays the selected annotation, or annotations, over the reference frame displayed on the display 336. To generate the reference frame data, a feature detector module 340 in the remote mentor system 330 may then detect image features in the reference frame in the neighborhood of the annotations. The image features are also referred to herein as "features" or "salient features," though that term does not imply any particular standard for determining salience, and may be automatically detected in the reference frame based on a predefined description such as pixel intensities. A descriptor extractor module 342 may then compute a respective signature, e.g., a unique signature, for each detected feature. The descriptor, in some examples, is a bit string that describes the pixel intensities at each pixel in an image patch surrounding a feature point. This allows comparing the descriptors from the reference frame to descriptors of future frames. The reference frame data, comprising the annotations, reference frame features, and associated descriptors, are then sent to the trainee system 310 via the communication network 320.

In the trainee system 310, a feature detector 344 detects image features of a current frame of the video stream being displayed on the display 316, and the features are enhanced with descriptors extracted by a descriptor extractor 346. A descriptor match module 348 matches the extracted current frame's descriptors with the corresponding reference frame's descriptors received from the remote mentor system 330 where the annotations were defined. Because the trainee's environment may change due to conditions such as the trainee system 310 being repositioned, the view field geometry changing, or the view field becoming partially occluded due to the surgeon's hands or newly added instruments, the comparison and matching of the reference and current frame features ensure that the annotations are placed and anchored to the intended areas of the view field defined by the mentor annotations. A homography relates any two images of the same planar surface in space and can be used to relate the reference image to the current image. A mapping module 350 may derive a homography for each annotation, and by using the derived homographies, transforms the annotations from the reference frame to the current frame. Techniques other than homography may be utilized to relate the reference and current images. An annotation rendering module 352 then renders the transformed annotations superimposed over the current frame displayed on the display 316. The annotation appears anchored to the view field.

To enhance the simulated transparency, the trainee system 310 may comprise a depth acquisition module 354 to obtain accurate geometry of the view field 106 to supplement the information obtained by the camera 314. The geometry information may be transmitted to the remote mentor's system 330 along with the reference image from the trainee's system 310 to enhance the reference frame data. For example, the feature detector module 340 of the remote mentor's system 330 may detect at least some of image features in the reference image relative to the annotation based, at least in part, on the geometry information. For example, features may be detected at corners or other points, such as edges, peaks, and valleys, with a high-magnitude spatial derivative of depth information. The depth acquisition module 354 may comprise a depth acquisition device such as a depth camera, a motion detector, an infrared depth sensor, or any other device or a combination of devices that are capable of acquiring accurate information of the geometry of the view field 106. The depth acquisition module 354 may be integrated in the trainee system 310. The trainee system 310 may additionally comprise a user tracking module 356 to adjust and re-project the images based on the trainee's view point for a better simulation of transparency. The tracking module 356 may include a plurality of user-facing cameras which may be used to triangulate the trainee's head position. The tracking module 356 may also be, or include, a depth acquisition device similar to the ones described above for the depth acquisition module 354. The tracking module 356 may be integrated in the trainee system 310, or may be an external module connected to the trainee system 310. As the trainee's view point changes, missing color samples, due to the limitations of the field of view and/or occlusion changes as the view-point changes from that of the video camera to that of the trainee, may be corrected by filling in the missing color samples with samples from older frames.

The trainee system and the remote mentor system may also include speaker-and-microphone sets, shown as set 358 for the trainee system and set 360 for the remote mentor system, to allow audio communications between the trainee 104 and the remote mentor 118.

The remote mentor system 330, in some examples, sends to the trainee system 310 only the type of annotations and their position in the reference frame. This compact encoding of annotations saves bandwidth and is sufficient to recreate the annotations at the trainee system based on a local copy of the set of sprites. In other examples, the remote mentor system 330 sends the types and positions of annotations, and also other information.

Applications of the enhanced remote collaboration system 300 is not limited to a surgical setting, and may be utilized in any remote instruction settings where interactions between a local operator, who is performing an act following instructions, and a remote instructor, who is providing the instructions and viewing the act as seen by the operator, are desirable. The ability to mark or annotate an object at the local operator's site and to follow the object and the annotation as seen by the operator is especially beneficial for hands-on training and instruction activities where the operator's act is dynamic and his view point may shift as the act progresses. Such training and instruction activities may include medical diagnostics, mechanical and/or electrical diagnostics and repairs, navigation where a route to a destination is annotated and updated, and other situations. The role of the remote instructor may also be realized with a computer program or artificial intelligence (AI) interacting with the local operator. With the AI as the remote instructor, the remote mentor's system 330 may be virtualized at a location accessible by the trainee's system 310 including memory in the trainee's system storing the instructions, when executed by the processor(s) 312, to realize the AI.

Figure 4:
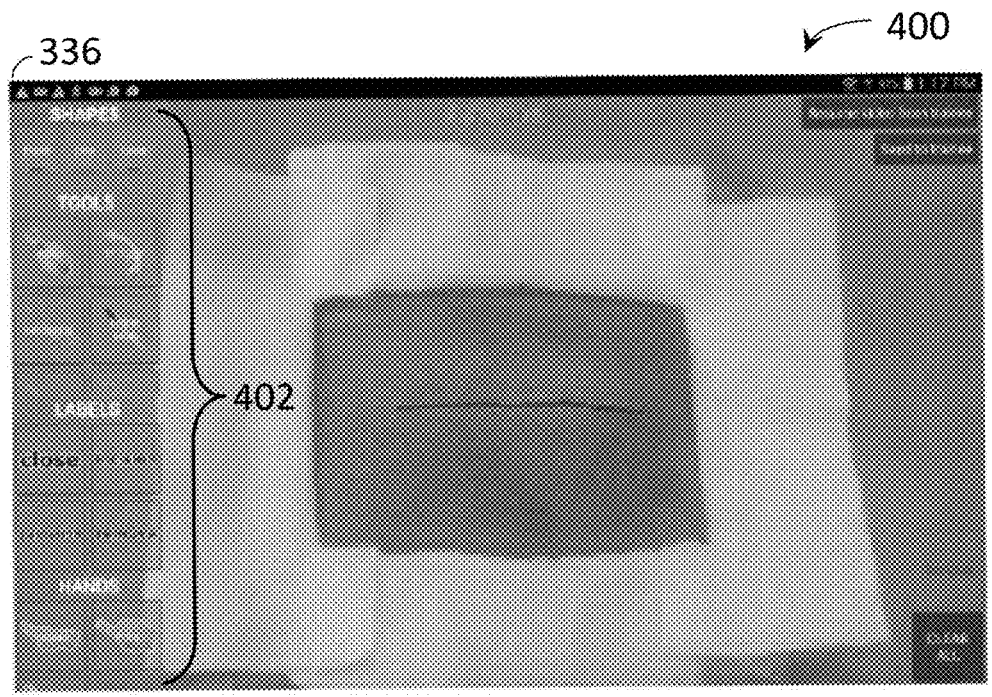
FIG. 4 is a graphical representation of an example annotation authoring interface as displayed on a remote mentor system in accordance with at least one aspect of the present disclosure.

FIG. 4 is an example block diagram 400 of an annotation module 338 of FIG. 3 as displayed on a remote mentor system in accordance with at least one aspect of the present disclosure. In this example embodiment, the annotation module 338 is shown as a user interface for a tablet with a touchscreen. The annotation module 338 may provide multiple selectable symbols such as icon-labeled buttons 402 on the display 336 of the remote mentor system 330. The selectable symbols may be selected by a mouse click, voice command, touch, or any other compatible user input mechanisms, e.g., input device 370, FIG. 3. The remote mentor 118 may tap to select a particular button of icon-labeled buttons 402. Each icon-labeled button may be associated with a predefined function and may be organized into various annotation categories.

Figure 5:
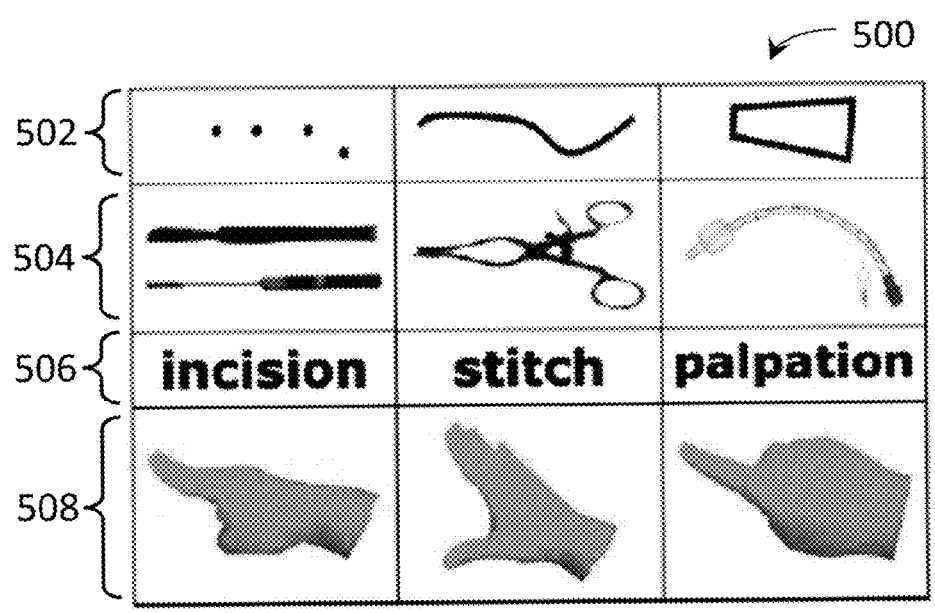
FIG. 5 is an example table of annotation categories in accordance with at least one aspect of the present disclosure.

FIG. 5 is an example table of annotation categories 500 in accordance with at least one aspect of the present disclosure. The categories may include drawing shapes 502, surgical tools 504, text labels 506, and hand gestures 508. The predefined text labels in the text labels 506 may include, e.g., "close," "incision," "palpation," "remove," and "stitch."

The types of drawing shapes in the drawing shapes 502 may include: points, lines, and polygons. Each shape may be defined with one or multiple points. In some examples, the mentor may draw on a touchscreen or tablet, draw by dragging with a mouse, or otherwise provide path information via an input device 370. The path information can include information of, e.g., at least one of location, pressure, direction, or duration of a user input. In the three columns of FIG. 5, the mentor can indicate an incision by drawing a series of points, and the path information can include the locations of those points. The mentor can indicate a stitch by drawing a line or curve, and the path information can include, e.g., the locations of Bezier control points in a decomposition of the drawn curve into at least one Bezier-curve segment. The mentor can indicate palpation by drawing a closed figure, such as a conic section or polygon, and the path information. These specific shapes are not limiting. For example, an incision can be indicated by a curve and a stitch can be indicated by a series of points. The mentor may also select and drag a certain button to indicate a desired operation.

The types of surgical tools the surgical tools 504 may include bag-valve-mask (BVM), endotracheal tube (ET), hemostat, iodine swab, longhook, retractor, scalpel, scissors, stethoscope, surgical tape, syringe, tweezers, and other surgical instruments.

The hand gesture annotations 508 illustrate typical manual actions performed by the surgeon and may include actions such as palpating, pointing, and stretching. Surgical tools, text labels, and hand gesture icons may be positioned based on a reference point, for example, the tip of the scalpel's blade. These selectable icons are displayed on the display 336 as an image with transparent background.

Figure 6:
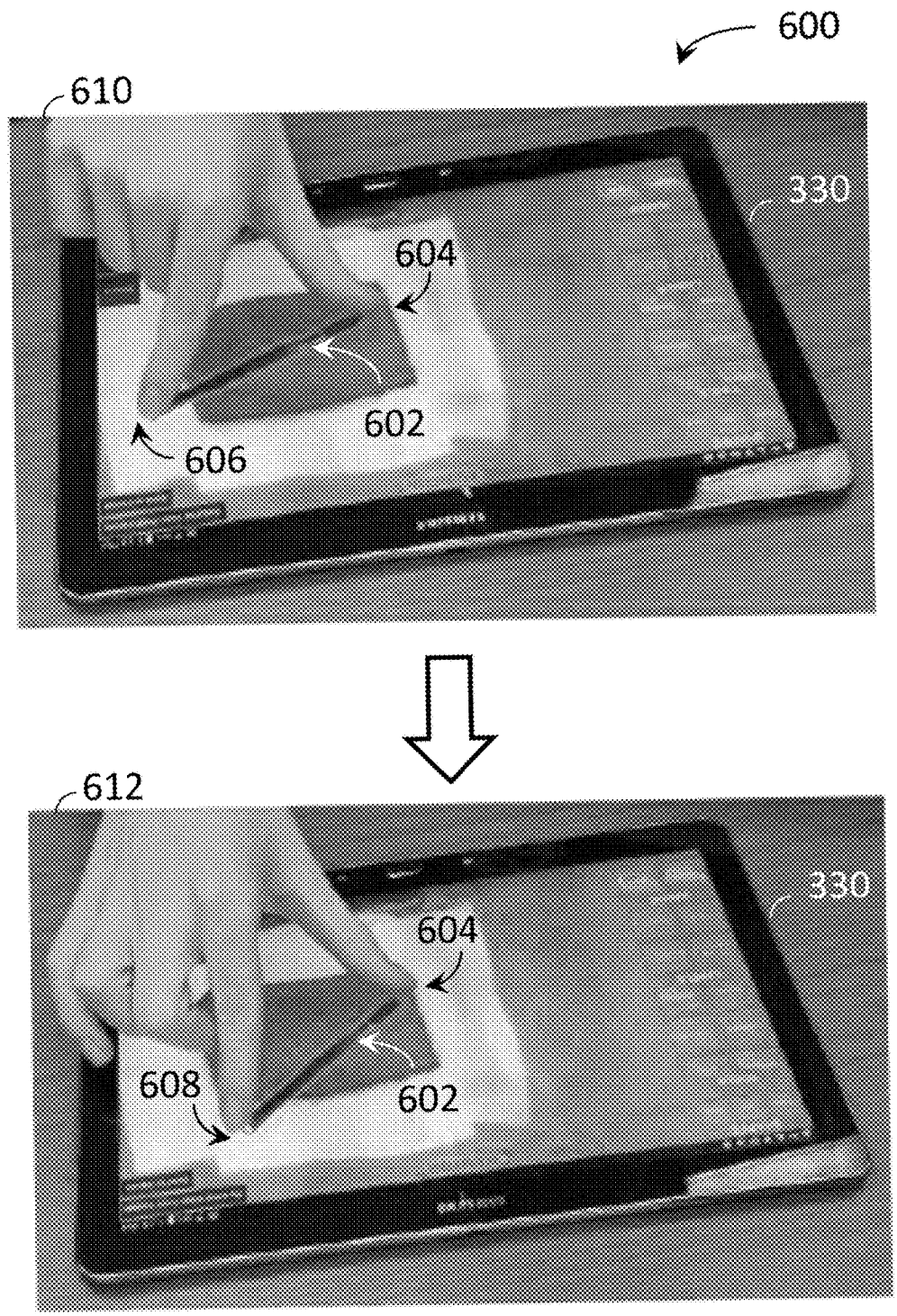
FIG. 6 is a graphical representation of an example diagram of the annotation orientation in the remote mentor system using a two-touch interaction orientation tool in accordance with at least one aspect of the present disclosure.

FIG. 6 is an example diagram 600 of the annotation orientation in the remote mentor system 330 using a two-touch interaction orientation tool in accordance with the present disclosure. Once selected, the annotation 602 may be positioned using a single-touch drag and drop interaction, and may be orientated using a two-touch interaction: one touch for defining the center of rotation 604 and the other touch for dragging motion for defining the rotation angle, shown as the starting point 606 and the ending point 608. The upper portion 610 shows the starting position of the annotation 602, from center of rotation 604 to starting point 606, and the lower portion 612 shows the ending position of the annotation 602, from center of rotation 604 to ending point 608.

Figure 7:
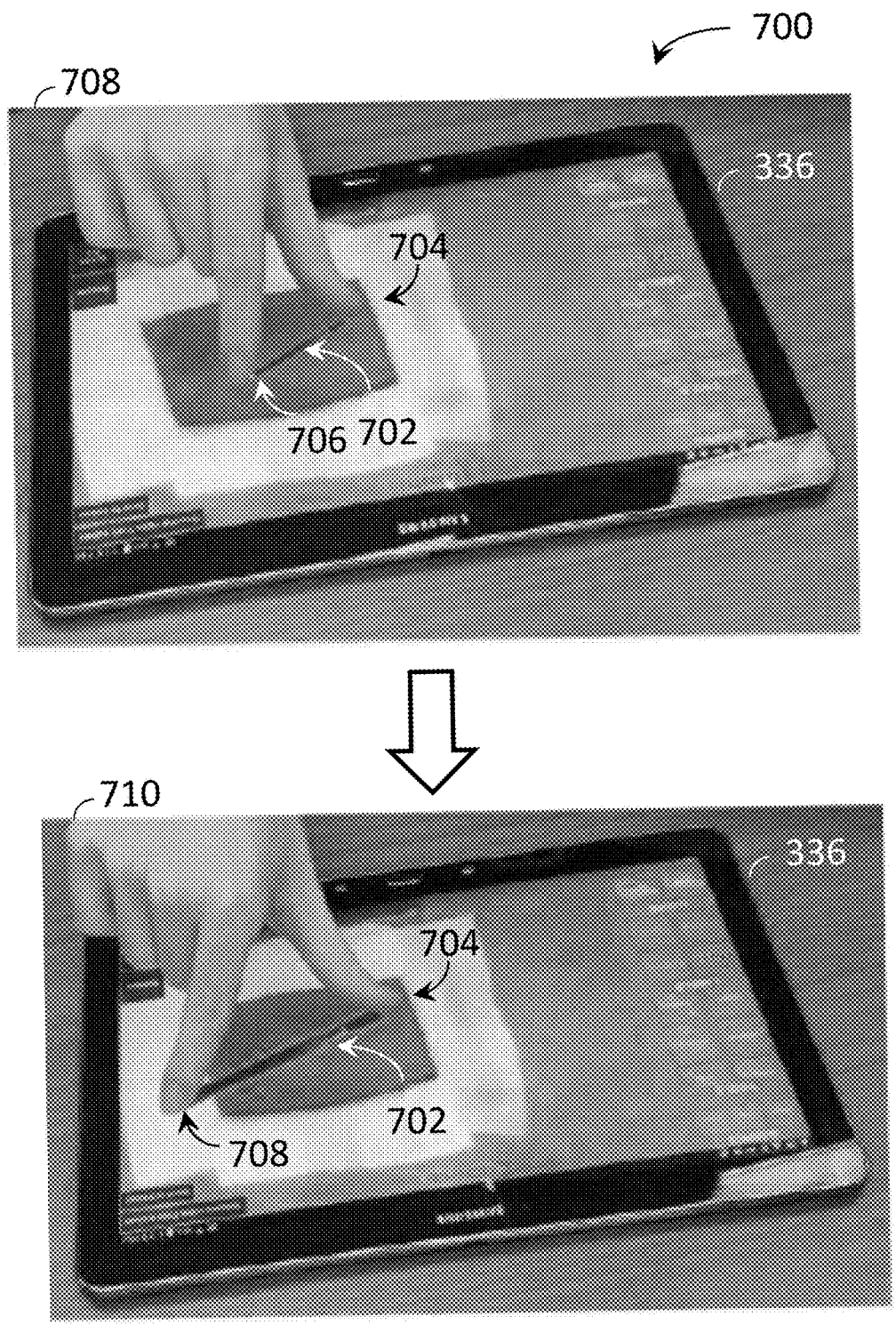
FIG. 7 is an example diagram of the annotation scaling in the remote mentor system using a two-touch interaction scaling tool in accordance with at least one aspect of the present disclosure.

FIG. 7 is an example diagram 700 of the annotation scaling using a two-touch interaction scaling tool in accordance with the present disclosure. Scaling of the annotation 702 may be performed by using a two finger pinch-and-zoom interaction: one finger for defining the fixed end of scaling 704 and the other finger for defining the starting point 706 and the ending point 708. The upper portion 708 shows the starting position of the annotation 702, from fixed end of scaling 704 to starting point 706, and the lower portion 710 shows the ending position of the annotation 702, from fixed end of scaling 704 to ending point 708.

Figure 8:
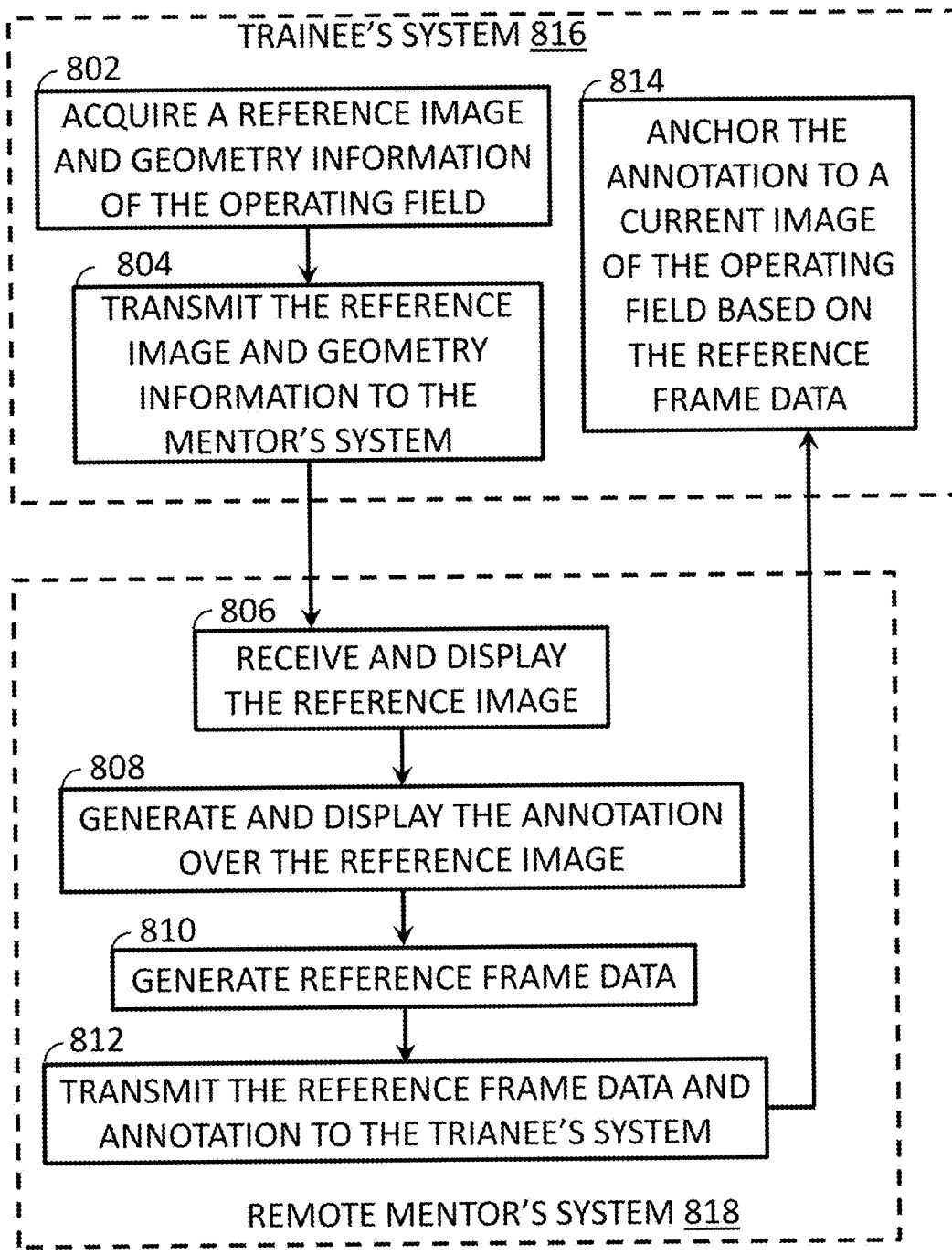
FIG. 8 is an example flowchart 800 of a process for providing anchored annotations over an image for enhancing remote collaboration utilizing a simulated transparent display with augmented reality in accordance with at least one aspect of the present disclosure.

FIG. 8 is an example flowchart 800 of a process in accordance with at least one aspect of the present disclosure. In some examples, the process is a process for providing anchored annotations over an image, e.g., for enhancing remote collaboration utilizing a simulated transparent display with augmented reality.

At block 802, a trainee's system 816 acquires a reference image and geometry information of operating view field and displays it on the trainee's system as described above with reference to the camera 314 and the depth acquisition module 354. At block 804, the trainee's system 816 transmits the reference image and the geometry information, as described above with reference to the transceiver 318, to the remote mentor's system via a communication network, as described above with reference to the communication network 320. The communication network may be any kind of communication network, wired or wireless, capable of communicating required data between the trainee system and the remote mentor system, such as cellular, Wi-Fi, Bluetooth, Ethernet communication networks and the like.

At block 806, the mentor's system 818 receives the reference image and geometry information and displays the reference image on the remote mentor's system as described above with reference to the transceiver 334 and the display 336. At block 808, the remote mentor's system 818 generates an annotation and displays over the reference image on the remote mentor's system as described above with reference to the annotation module 338. The annotation may be received via a user interface such as a selectable icon with a predefined annotation as described in FIGS. 4 and 5. At block 810, the remote mentor's system 818 generates reference frame data based on the reference image, the geometry information, and the annotation as described above with reference to the feature detector module 340 and the descriptor extractor 342. The reference frame data may be generated from detecting a plurality of salient features in the reference image relative to the annotation and computing a descriptor for each of the plurality of the salient features. At block 812, the remote mentor's system 818 transmits the reference frame data and annotation to the trainee's system via the communication network as described above with reference to the transceiver 334.

At block 814, the trainee's system 816 anchors the annotation to a current image of the view field based on the reference frame data received. To anchor the annotation to the current image, the trainee's system 816 may detect a plurality of salient features in the current image of the view field displayed on the first display device as described above with reference to the feature detector 344, compute a descriptor for each of the plurality of the salient features in the current image as described above with reference to the descriptor extractor 346, and match the current image descriptors with the reference image descriptors as described above with reference to the descriptor match module 348. The trainee's system 816 may then derive a homography or other mapping for the annotation based on the matched descriptors, transform the annotation from the reference image to the current image based on the derived homography as described above with reference to the mapping module 350, and render the transformed annotation over the current image displayed on the trainee's system as described above with reference to the annotation rendering module 352.

In the illustrated example, blocks 802, 804, and 814 are included in a trainee's system 816. In the illustrated example, blocks 806, 808, 810, and 812 are included in a mentor's system 818. In some examples, systems 816 and 818 are physically spaced apart from each other. e.g., within a room such as an operating room, in different rooms in a building such as a teaching hospital, or in different buildings (e.g., during a telesurgery session).

As the trainee's system is repositioned, as the view field geometry changes, and/or as the view field becomes partially occluded due to the surgeon's/trainee's hands and due to new instruments added to the view field, the annotations have to be repositioned to remain overlaid onto the associated view field elements. To compensate for these changes, the trainee's system may track a position of a view point of the trainee, such as the position of head or eyes, as described above with reference to the tracking module 356, and adjust the reference image of the view field based on the position of the view point of the trainee and the geometry information as described above with reference to the depth acquisition module 354, such that a new image of the view field displayed on the first display device continues to represent a view of the view field by the trainee.

Annotation anchoring is performed in two major stages, in some examples. The first stage preprocesses the reference frame where annotations are defined to prepare for annotation anchoring in future frames. The second stage uses the preprocessed reference frame and processes the current frame to anchor the annotation.

Figure 9:
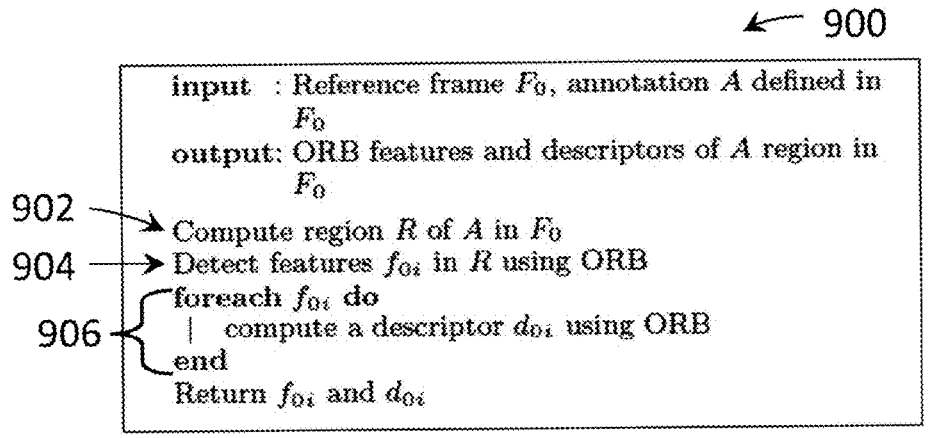
FIG. 9 is an example reference frame preprocessing algorithm in accordance with at least one aspect of the present disclosure.

FIG. 9 is an example reference frame preprocessing algorithm 900 in accordance with at least one aspect of the present disclosure.

At step 902, the region R of the annotation is defined with an axis aligned rectangle that is obtained by enlarging the 2D axis aligned bounding box of the annotation. R would be a rectangle that surrounds the area of interest such as the view field 106. At step 904 as described above with reference to the feature detector module 340, feature points are identified in the region R using the ORB (Oriented FAST (Features from Accelerated Segment Test) and Rotated BRIEF (Binary Robust Independent Elementary Features)) feature detection algorithm, which uses FAST feature detection along with image pyramids to find multiscale features. At step 906, a descriptor is computed for each feature point using the ORB descriptor extraction algorithm as described above with reference to the descriptor extractor 342. The descriptor is a bit string that describes the pixel intensities at each pixel in an image patch surrounding the keypoint, in some examples. This allows comparing the descriptors from the reference frame to descriptors of future frames, for example, from the reference frame to the current image. The annotation with its set of descriptors is sent to the trainee system 310 where the annotation is tracked and displayed.

Figure 10:
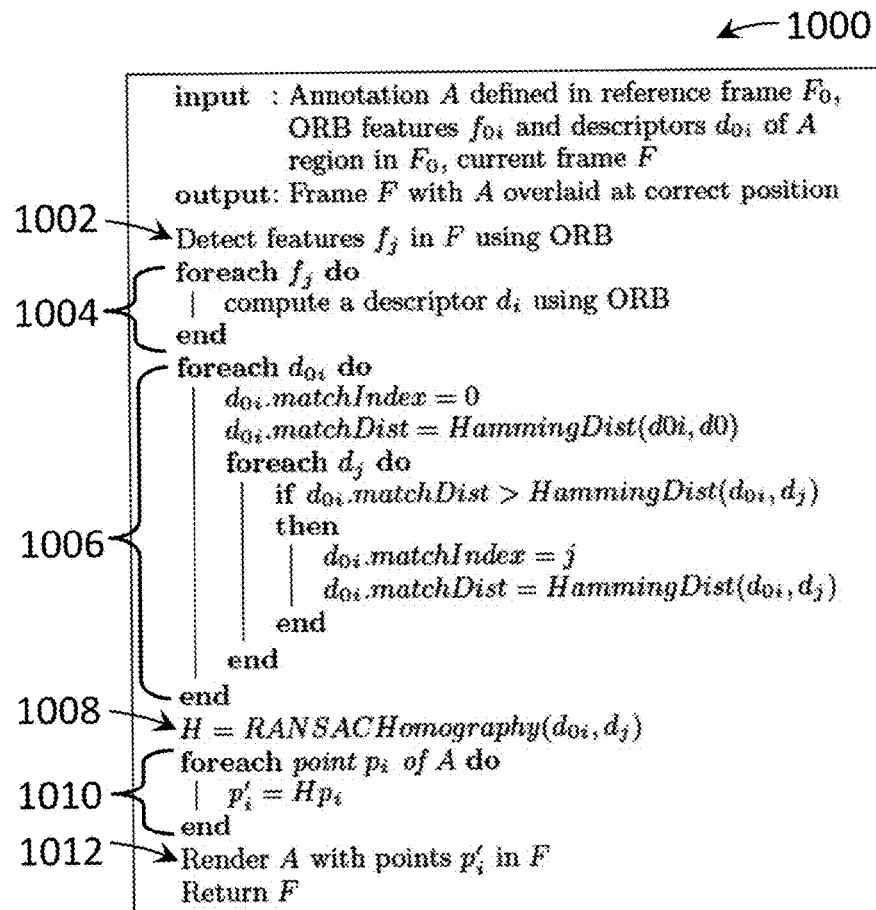
FIG. 10 is an example annotation anchoring algorithm in accordance with at least one aspect of the present disclosure.

FIG. 10 is an example annotation anchoring algorithm 1000 in accordance with at least one aspect of the present disclosure. The current frame is first processed similarly to the reference frame: at step 1002, features are detected as described above with reference to the feature detector 344, and then at step 1004, enhanced with descriptor data as described above with reference to the descriptor extractor 346. For some features near the edges of the frame, descriptor computation may fail. Because descriptor extraction, in some examples, involves reading the intensities of pixels in a ring surrounding the feature, if that ring extended beyond the edges of the image, there would be insufficient information to complete the descriptor extraction. Features for which descriptor computation fails may be omitted from further processing of the features of the respective image.

Next, at step 1006, the reference frame's descriptors are matched to the current frame's descriptors using an all-pairs brute-force matching algorithm as described above with reference to the descriptor match module 348. Each reference frame descriptor $d_{0i}$ is matched against each current frame descriptor $d_j$, selecting the match with the lowest Hamming distance between the descriptors. The matched descriptors are used to define a homography H, as described above with reference to the mapping module 350, from the reference frame to the current frame using a RANSAC (RANdom SAmple Consensus)-based algorithm at step 1008. A RANSAC-based algorithm permits estimating parameters from a set of observed data which contains outliers and determining matching points between the reference frame and the current image. In some examples, this homography computation method takes as one of its parameters a reprojection threshold, which determines whether a match is considered to be an inlier or an outlier. This threshold value is scaled based on the downsample factor of the input frame; otherwise, a smaller image with a relatively larger reprojection threshold would allow too many outliers to find a good homography. H maps a reference frame point to a current frame point. At step 1010, the homography is applied to each annotation point pi, positioning the annotation in the current frame as described above with reference to the mapping module 350. Finally, at step 1012, the annotation is rendered with F as background at the position defined by the transformed points poi as described above with reference to the annotation rendering module 352.

FIG. 1 is an example keypoint matching algorithm 1100 in accordance with at least one aspect of the present disclosure. When the remote mentor selects a reference image, or template, the system may automatically detect the image features in the template, or reference, image as A at step 1102 (Line 1 of the algorithm 1100), e.g., as described above with reference to the feature detector module 340, 344. The locations of those image features are saved as T in step 1104 (Line 2 of the algorithm 1100) along with the annotation points. A, made on the reference image. Then, in step 1106 (Line 3 of the algorithm 1100), for each iteration of the computational thread, a subsequent image has its feature points likewise detected and stored in a second keypoint array S. At step 1108 (Lines 4-9 of the algorithm 1100), each of the sets are compared to find matching sets between the two keypoint arrays, T and S, e.g., as described above with reference to the descriptor match module 348. At step 1110 (Lines 10-12 of the algorithm 1100), an array M of matching indexes is generated, and the algorithm 1100 ends at step 1112 (Line 13 of the algorithm 1100).

FIG. 12 is an example parameter extraction algorithm 1200 in accordance with at least one aspect of the present disclosure. Using the set of matches M, along with T and S, the algorithm 1200 finds the changes in pan shift, rotation, and scale between two images. The algorithm 1200 starts at step 1202 (Line 1 of the algorithm 1200). At step 1204 (Lines 2-8 of the algorithm 1200), for each cloud of matched keypoints, the distances between every point pair, $D_T$ and $D_S$, and the difference in angles between each corresponding point pair across θ is determined. In step 1206 (Lines 9 and 10 of the algorithm 1200), the ratio r of sizes between the template and current scene comes from the median distances in $D_T$ and $D_S$. In step 1208 (Lines 11-13 of the algorithm 1200), the system then finds the centroids of each of the matched points clouds. All these values are used to find the projection locations of the annotations P by applying Equation 1210 to each of k annotation points as described above with reference to the mapping module 350.

Figure 13:
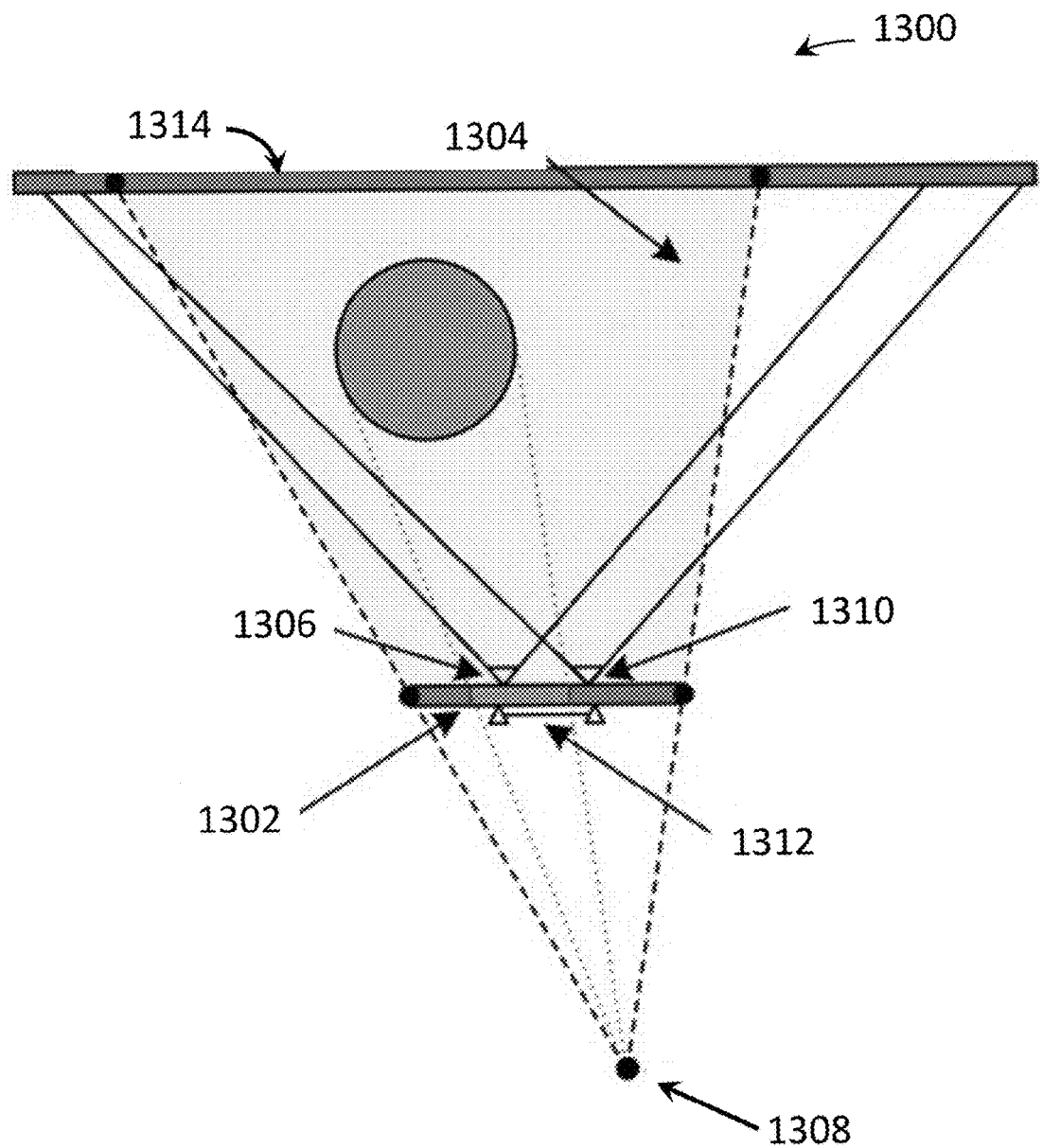
FIG. 13 is an example setup for a simulated transparent display in accordance with at least one aspect of the present disclosure.

FIG. 13 is an example setup 1300 for a simulated transparent display in accordance with at least one aspect of the present disclosure. To simulate a transparent display, such as the display 316 of the trainee's device 310, using a conventional liquid crystal display (LCD) 1302 or other electronic display, the image that the user would see in the absence of the display 1302 needs to be displayed. The display occlusion shadow 1304, the part of the scene obstructed by the LCD 1302, may be captured with a camera 1306. Placing the camera 1306 at the user's viewpoint 1308 may not beneficial because the camera's view would also be obstructed by the LCD, in addition to the disadvantage of the user having to wear the camera. Consequently, the camera 1306 may need to be placed at a different viewpoint, beyond the LCD 1302, such that the scene would be captured without occlusions. The frame captured by the camera 1306 would then be reprojected to the user's viewpoint 1308, which requires knowledge of scene geometry.

Some parts of the scene in the display occlusion shadow 1304 may be acquired with a color camera 1306 and a depth camera 1310, e.g., as described above with reference to the camera 314 and a depth acquisition module 354. The color camera 1306 and the depth camera 1310 may be fixed with respect to each other, and their relative position and orientation may be pre-calibrated, e.g., using a black and white checkerboard that is seen by both cameras, or other predetermined test targets. Depth may also be acquired in a real-time by the depth camera 1310. Depth information is then used to triangulate the image plane 1314 or otherwise determine a mesh or other computational representation of surfaces included in the display occlusion shadow 1304. The user's viewpoint 1308 may be acquired with a tracker 1312 that triangulates the position of the user's head as described above with reference to the tracking module 356. The color and depth data may then be rendered from the user's viewpoint 1308 to simulate transparency. For example, the color data may be texture-mapped over polygons (e.g., triangles) or other surfaces in the computational representation of the surfaces.

EXAMPLE CLAUSES

A: A method for enhancing remote collaboration, comprising superimposing at least one annotation onto an image of the real world using an augmented reality transparent (ART) display.

B: The method of paragraph A, wherein the ART display is suspended into a user's field of view.

C: The method of paragraph A or B, wherein the ART display is mounted on a user's head.

D: The method of any of paragraphs A-C, wherein the ART display is implemented using a tablet computer and its video camera.

E: The method of any of paragraphs A-D, wherein the ART display is implemented using a tablet computer and its video camera, a head tracker, and a depth camera.

F: The method of any of paragraphs A-E, wherein the ART display is implemented with a physically transparent display, e.g. a transparent OLED.

G: The method of any of paragraphs A-F, wherein the ART display is mounted using at least one of a mechanical arm or a robotic arm.

H: The method of any of paragraphs A-G, wherein at least one annotation is anchored to the real-world entity it describes, as the real world changes, as the user head moves, and as the ART display is repositioned.

I: The method of any of paragraphs A-H, wherein the annotations are generated through embodied interaction (e.g. gestures) and anchored using an algorithm comprising the features of: generating the annotations in an initial image using translation, scaling, and rotation; establishing a mapping between the initial image and a new image; positioning the annotations in the new image by transforming the position of the annotations in the initial image using the mapping between the initial and the new images.

J: The method of paragraph I, further comprising matching a plurality of features in the new image with a plurality of initial features in the initial image.

K: The method of any of paragraphs A-J, wherein the remote collaboration is telementoring.

L: The method of any of paragraphs A-K, wherein the remote collaboration is surgical telementoring.

M: The method of any of paragraphs A-L, wherein the remote collaboration is remote instruction.

N: The method of any of paragraphs A-M, further comprising communicating between at least two parties.

O: The method of any of paragraphs A-N, wherein the at least two parties comprise a human party and artificial party.

P: The method of any of paragraphs A-O, wherein the at least two parties comprise at least two human parties.

Q: The method of any of paragraphs A-P, further comprising orienting the annotations based at least in part on that a geometric transformation and a current frame.

CONCLUSION

Although the techniques have been described in language particular to structural features or methodological acts, it is to be understood that the appended claims are not necessarily limited to the features or acts described. Rather, the features and acts are described as example implementations of such techniques.

All of the methods and processes described above can be embodied in, and fully automated via, software code modules executed by one or more general purpose computers or processors. The code modules can be stored in any type of computer-readable storage medium or other computer storage device. Some or all of the methods can be embodied in specialized computer hardware.

Conditional language such as, among others. "can," "could," "might" and/or "may," unless specifically stated otherwise, are understood within the context to present that certain examples include, while other examples do not include, certain features, elements and/or steps. Thus, such conditional language is not generally intended to imply that certain features, elements and/or steps are in any way required for one or more examples and/or that one or more examples necessarily include logic for deciding, with and/or without user input and/or prompting, whether certain features, elements and/or steps are included and/or are to be performed in any particular example. The word "or" and the phrase "and/or" are used herein in an inclusive sense unless specifically stated otherwise. Accordingly, conjunctive language such as the phrases "X, Y, or Z," "X, Y, and/or Z," "at least X, Y, or Z," or "at least one of X. Y or Z," unless specifically stated otherwise, is to be understood as signifying that an item, term, etc., can be either X, Y, or Z, or a combination thereof.

The disclosure includes combinations of the examples described herein. References to a particular "example" and the like refer to features that are present in at least one example or configuration of what is within the scope of the disclosed subject matter. Separate references to "an example" or "particular examples" or the like do not necessarily refer to the same example or examples; however, such examples are not mutually exclusive, unless specifically indicated. The use of singular or plural in referring to "example," "examples," "method," "methods" and the like is not limiting. Moreover, in the claims, any reference to a group of items provided by a preceding claim clause is a reference to at least some of the items in the group of items, unless specifically stated otherwise.

Various embodiments of the present disclosure have been described in detail with particular reference to certain preferred aspects thereof, but it will be understood that variations, combinations, and modifications can be effected by a person of ordinary skill in the art within the spirit and scope of the disclosure.

What is claimed is:

1. A system comprising:
   a first computing device, the first display device comprising:
      a first processor;
      a first camera coupled to or operable by the first processor, the first camera configured to capture a reference image and a current image of a view field;
      a display configured to display the current image;
      a depth acquisition module coupled to or operable by the first processor, the depth acquisition module configured to acquire geometry information of the view field; and
      a first transceiver coupled to or operable by the first processor, the first transceiver configured to:
         transmit the reference image and the geometry information; and
         receive annotation information to be displayed on the first display; and
   a second computing device communicatively connectable with the first computing device, the second computing device comprising:
      a second processor;
      a user-operable input device coupled or operable by to the second processor;
      a second transceiver coupled or operable by to the second processor, the second transceiver configured to receive the reference image and the geometry information from the first computing device;
      an annotation module coupled to or operable by the second processor to receive input via the input device and determine at least one annotation based at least in part on the input; and
      a second display coupled to or operable by the second processor, the second display configured to display the reference image and to display the at least one annotation superimposed over the reference image,
   wherein:
      the second transceiver is further configured to transmit reference frame data to the first computing device, the reference frame data associated, at least in part, with the reference image, the geometry information, and the at least one annotation; and
      the first computing device is further configured to display the at least one annotation anchored to the displayed current image based on the received reference frame data.

2. The system of claim 1, wherein the annotation module is further configured to display a plurality of selectable symbols on the second display, each of the plurality of selectable symbols associated with a predefined annotation.

3. The system of claim 1, wherein the second computing device further comprises:
   a reference feature detector module coupled to or operable by the second processor, the reference feature detector configured to detect a plurality of image features in the reference image relative to the at least one annotation based, at least in part, on the geometry information; and
   a reference descriptor extractor module coupled to or operable by the second processor, the reference descriptor extractor module configured to determine a descriptor for each of the plurality of the image features, wherein the reference frame data comprises at least some of the descriptors of the reference image.

4. The system of claim 3, wherein the first computing device further comprises:

a current feature detector module coupled to or operable by the first processor, the current feature detector configured to detect a plurality of image features in the current image of the view field;

a current descriptor extractor module coupled to or operable by the first processor, the current descriptor extractor module configured to compute a descriptor for each of the plurality of the image features in the current image;

a descriptor matching module coupled to or operable by the first processor, the descriptor matching module configured to match at least some of the current image descriptors with at least some of the reference image descriptors to provide match information;

a mapping module coupled to or operable by the first processor, the mapping module configured to:
  determine a mapping for the annotation based on the match information, and
  transform the annotation from the reference image to the current image based on the determined mapping; and an annotation rendering module coupled to or operable by the first processor, the annotation rendering module configured to render the transformed annotation over the current image displayed on the first display.

5. The system of claim 4, wherein the first computing device further comprises:

a tracking module coupled to or operable by the first processor, the tracking module configured to:
  determine a position of a view point of a user of the first computing device; and
  determine an updated image of the view field based at least in part on the current image of the view field, the geometry information, and the position of the view point of the user;

wherein the first computing device is configured to display on the first display the updated image of the view field.

6. The system of claim 5, wherein the tracking module comprises at least one of:
  at least one camera facing the user, or
  a depth measurement device facing the user.

7. The system of claim 5, wherein the tracking module is further configured to determine a position of the first computing device relative to the view point of a user and to determine the updated image further based on the position of the first computing device and the geometry information.

8. A method comprising:
  acquiring a reference image and geometry information of operating view field by a first computing device;
  transmitting the reference image from the first computing device to a second computing device;
  displaying the reference image at the second computing device;
  determining an annotation at the second computing device;
  displaying the annotation over the reference image on a display of at the second computing device;
  generating reference frame data at the second computing device based, at least in part, on the reference image, the geometry information, and the annotation, the reference frame data comprising information associated with a plurality of image features in the reference image;
  transmitting the reference frame data and the annotation from the second computing device to the first computing device;
  receiving the reference frame data and the annotation by the first computing device;
  acquiring a current image of the view field by the first computing device;
  determining a position of the annotation in the current image based on the reference frame data;
  displaying the current image on a display of the first computing device; and
  displaying the annotation over the current image at the determined position on the display of the first computing device.

9. The method of claim 8, wherein the determining the annotation comprises at least one of:
  receiving path information via a user-operable input device of the second computing device and determining the annotation based at least in part on the path information;
  displaying a plurality of symbols on the display of the second computing device and receiving, via the input device, a selection of a symbol of the plurality of symbols and determining the annotation as a predefined annotation associated with the symbol; or
  receiving textual input via the input device and determining the annotation based at least in part on the textual input.

10. The method of claim 8, wherein the generating the reference frame data comprises:
  detecting at least some of the plurality of image features in the reference image relative to the annotation based, at least in part, on the geometry information; and
  determining the information including a descriptor for each of the at least some of the plurality of the image features.

11. The method of claim 10, wherein determining the position of the annotation comprises:
  detecting a plurality of image features in the current image of the view field;
  computing a descriptor for each of the plurality of the image features in the current image;
  matching the current image descriptors with the reference image descriptors to provide match information;
  deriving a mapping for the annotation based on the match information; and
  determining the position of the annotation based at least in part on the derived mapping.

12. The method of claim 11, further comprising:
  determining second reference frame data based at least in part on the current image;
  acquiring a second current image; and
  determining a second position of the annotation in the second current image based at least in part on the second reference frame data.

13. The method of claim 8, further comprising displaying the reference image of the view field on the display of the first computing device, wherein the displayed reference image appears as a direct view of the view field by a user.

14. The method of claim 8, further comprising:
determining a position of a view point of a user;
determining an updated image based at least in part on the current image, the geometry information, and the position of the view point; and
displaying the updated image on the display of the first computing device.

15. The method of claim 14, wherein the determining the position of the view point of the user comprises:
capturing an image using at least one camera associated with the first computing device facing the user, or
capturing a depth image using a depth measurement device associated with the first computing device facing the user.

16. The method of claim 8, further comprising:
determining a position of the first computing device;
determining an updated image based at least in part on the current image, the position of the first computing device, and the geometry information; and
displaying the updated image on the display of the first computing device.

17. One or more non-transitory computer-readable media storing instructions that are executable by one or more processors to cause a computing system to:
acquire a reference image and geometry information of a view field;
transmit the reference image and the geometry information via a communications interface;
receive reference frame data and an annotation via the communications interface;
acquire a current image of the view field;
determine a position of the annotation in the current image of the view field based on the reference frame data and geometry information; and
display the annotation over the current image at the determined position on a computing device.

18. The one or more non-transitory computer-readable media of claim 17, wherein the instructions are further executable by the one or more processors to cause the computing system to:
detect a plurality of image features in the reference image relative to the annotation, based at least in part, on the geometry information;
determine a descriptor for each of the plurality of the image features in the reference image;
detect a plurality of image features in the current image;
determine a descriptor for each of the plurality of the image features in the current image;
match at least some of the current image descriptors with the reference image descriptors to provide match information;
derive a mapping for the annotation based on the match information;
transform the annotation from the reference image to the current image based on the derived mapping; and
render the transformed annotation over the current image displayed on the computing device.

19. The one or more non-transitory computer-readable media of claim 18, wherein the instructions are further executable by the one or more processors to cause the computing system to:
determine a position of a view point of a user;
determine an updated image based at least in part on the current image, the geometry information, and the position of the view point; and
display the updated image on the computing device.

20. The one or more non-transitory computer-readable media of claim 18, wherein the instructions are further executable by the one or more processors to cause the computing system to:
determine a position of the computing device;
determine an updated image based at least in part on the current image, the position of the first computing device, and the geometry information; and display the updated image on the computing device.

* * * * *